(12) United States Patent
Kotanko et al.

(10) Patent No.: US 11,426,503 B2
(45) Date of Patent: Aug. 30, 2022

(54) ARTERIOVENUS FISTULA MATURATION MONITORING SYSTEMS AND METHODS

(71) Applicant: Fresenius Medical Care Holdings, Inc., Waltham, MA (US)

(72) Inventors: Peter Kotanko, New York, NY (US); Stephan Thijssen, New York, NY (US); Hanjie Zhang, New York, NY (US); Israel Campos, New York, NY (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 653 days.

(21) Appl. No.: 16/249,768

(22) Filed: Jan. 16, 2019

(65) Prior Publication Data

US 2020/0222618 A1    Jul. 16, 2020

(51) Int. Cl.
  *A61M 1/36*   (2006.01)
  *A61M 1/16*   (2006.01)
  *A61B 5/145*  (2006.01)

(52) U.S. Cl.
  CPC ............ *A61M 1/3656* (2014.02); *A61M 1/16* (2013.01); *A61M 1/3655* (2013.01); *A61B 5/14542* (2013.01); *A61M 2205/18* (2013.01); *A61M 2205/50* (2013.01); *A61M 2230/20* (2013.01); *A61M 2230/207* (2013.01)

(58) Field of Classification Search
  CPC .............. A61M 1/3656; A61M 1/3655; A61M 2205/18; A61M 2230/20; A61B 5/14542
  See application file for complete search history.

(56) References Cited

U.S. PATENT DOCUMENTS

2013/0012861 A1   1/2013   Zhang
2016/0310077 A1   10/2016  Hunter et al.

FOREIGN PATENT DOCUMENTS

WO   2015108928 A1   7/2015

OTHER PUBLICATIONS

International Search Report and Written Opinion for International application No. PCT/US2020/013666, dated May 8, 2020, 15 pages.
Rosales, L., et al., "Tracking Arteriovenous Fistula Maturation: A Novel Approach", Blood Purification 47(1-3):240-245 (2018).

*Primary Examiner* — Leslie R Deak
(74) *Attorney, Agent, or Firm* — KDB (57) ABSTRACT

Techniques and systems for determining an arteriovenous (AV) fistula maturation in a patient may include detecting a first series of oxygen saturation levels of the patient at a central venous catheter (CVC) associated with a first series of hemodialysis treatments prior to the AV fistula implantation are described. The AV fistula may then be implanted in the patient. A second series of oxygen saturation levels of the patient at the CVC associated with a second series of hemodialysis treatments may be detected. The second series of oxygen saturation levels may be compared to a stable threshold mature AV fistula oxygen saturation level. Among other determinations from the comparison, in response to one or more of the second series of oxygen saturation levels meeting or exceeding the stable threshold mature AV fistula oxygen saturation level, determining the AV fistula is mature. Other embodiments are described.

22 Claims, 5 Drawing Sheets

ARTERIOVENUS FISTULA MATURATION MONITORING SYSTEMS AND METHODS

TECHNICAL FIELD

The disclosure generally relates to an arteriovenous (AV) fistula procedure in a dialysis treatment process, and, more particularly, to AV fistula maturation monitoring systems and methods.

BACKGROUND

For patients undergoing hemodialysis treatment, dialysis may be performed temporarily via a central-venous catheter (CVC), although there may exist a need for long-term access to an artery for treatment, thereby achieving greater patient comfort and ease of access. Typically, an arteriovenous connection, or arteriovenous (AV) fistula, may be implanted to connect an artery to a vein for receiving dialysis treatment. However, after implantation, the AV fistula must mature for a period of time to allow the blood flow rate to equalize. As an artery is a high blood flow pressure, and a vein is typically a lower blood flow pressure, after an AV fistula is connected the vein may swell while accommodating a flow from the high-pressure source (artery) to the low-pressure source (vein) until reaching equilibrium.

Typically, a medical professional may determine when an AV fistula has matured enough for the patient to receive dialysis treatment through the AV fistula, based off a visual examination and their level of experience. For example, the medical professional may evaluate the AV fistula clinically by palpation and auscultation. This subjective evaluation may result in adverse health effects for the patient if the medical professional makes an error in the maturation determination. The medical professional may also use existing systems, such as Doppler ultrasound or angiography for verification, but these systems are time consuming, and may not be regularly available for use by the medical professional. In addition, using angiography may be invasive for a patient already receiving serious medical treatment.

The current systems and methods for determining AV fistula maturation have several potential drawbacks. For example, if the AV fistula has not matured for a long enough time period and is used prematurely, the AV fistula may not allow for enough blood flow, or in some instances, may collapse. Conversely, a patient may be required to wait an unnecessarily long time period, if the AV fistula maturation time period is overestimated, requiring the patient to continue receiving treatment via the central venous catheter (CVC) for longer than necessary. Additionally, failures in the AV fistula may be not be detected in a timely manner, for example, failure of remodeling of the artery and vein. In some extreme instances, the medical professional may even forget the patient has received a AV fistula and fail to evaluate it altogether.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

In accordance with various aspects of the described embodiments is a method for determining an arteriovenous (AV) fistula maturation in a patient. The method may include detecting a first series of oxygen saturation levels of the patient at a central venous catheter (CVC) associated with a first series of hemodialysis treatments prior to the AV fistula implantation, implanting the AV fistula in the patient, detecting a second series of oxygen saturation levels of the patient at the CVC associated with a second series of hemodialysis treatments, and comparing the second series of oxygen saturation levels to a stable threshold mature AV fistula oxygen saturation level, wherein in response to one or more of the second series of oxygen saturation levels meeting or exceeding the stable threshold mature AV fistula oxygen saturation level, determining the AV fistula is mature.

In some embodiments of the method, the detected first series of oxygen saturation levels are recorded by a blood monitoring system. In various embodiments of the method, the detected second series of oxygen saturation levels are recorded by a blood monitoring system. In some embodiments of the method, the first series of oxygen saturation levels include one or more measurements corresponding to a hemodialysis treatment in the first series of hemodialysis treatments. In various embodiments of the method, the second series of oxygen saturation levels include one or more measurements corresponding to a hemodialysis treatment in the second series of hemodialysis treatments. In exemplary embodiments of the method, in response to a progression of the one or more measurements of the second series of oxygen saturation levels at least one of decreasing, non-stabilizing, or stabilizing below the stable threshold mature AV fistula oxygen saturation level, issuing an alert of a failure of the AV fistula. In various embodiments of the method, in response to a progression of the one or more measurements of the second series of oxygen saturation levels increasing, and the second series of oxygen saturation levels are greater than the first series of oxygen saturation levels, validating a maturation of the AV fistula over time. In some embodiments of the method, in response to the second series of oxygen saturation levels being lower than the first series of oxygen saturation levels, issuing an alert of a failure of the AV fistula. In various embodiments of the method, the method may further include monitoring the second series of oxygen saturation levels for at least one of a stabilization or a plateau. In some embodiments of the method, the stable threshold mature AV fistula oxygen saturation level is determinable by at least one of clinical data and mathematical modeling. In various embodiments of the method, the at least one of the clinical data and the mathematical modeling predict an approximate time of when the AV fistula has matured.

In accordance with various aspects of the described embodiments is a system for determining an arteriovenous (AV) fistula maturation in a patient. The system may include a hemodialysis machine, a blood monitoring system, the blood monitoring system being configured to detect a first series of oxygen saturation levels of the patient at a central venous catheter (CVC) associated with a first series of hemodialysis treatments prior to the AV fistula implantation, detect a second series of oxygen saturation levels of the patient at the CVC associated with a second series of hemodialysis treatments after the AV fistula implantation, and compare the second series of oxygen saturation levels to a stable threshold mature AV fistula oxygen saturation level, wherein in response to one or more of the second series of oxygen saturation levels meeting or exceeding the stable threshold mature AV fistula oxygen saturation level, determining the AV fistula is mature In some embodiments of the system, the detected first series of oxygen saturation levels are recordable by the blood monitoring system. In various embodiments of the system, the detected second series of oxygen saturation levels are recordable by the blood monitoring system. In some embodiments of the system, the first series of oxygen saturation levels include one or more measurements corresponding to a hemodialysis treatment in the first series of hemodialysis treatments. In various embodiments of the system, the second series of oxygen saturation levels include one or more measurements corresponding to a hemodialysis treatment in the second series of hemodialysis treatments. In some embodiments of the system, in response to a progression of the one or more measurements of the second series of oxygen saturation levels at least one of decreasing, non-stabilizing, or stabilizing below the stable threshold mature AV fistula oxygen saturation level, issuing an alert of a failure of the AV fistula. In exemplary embodiments of the system, in response to a progression of the one or more measurements of the second series of oxygen saturation levels increasing, and the second series of oxygen saturation levels are greater than the first series of oxygen saturation levels, validating a maturation of the AV fistula over time. In various embodiments of the system, in response to the second series of oxygen saturation levels being lower than the first series of oxygen saturation levels, sending an alert of a failure of the AV fistula. In some embodiments of the system, the blood monitoring system may be further configured to monitor the second series of oxygen saturation levels for at least one of a stabilization or a plateau. In various embodiments of the system, the stable threshold mature AV fistula oxygen saturation level is determinable by at least one of clinical data and mathematical modeling. In some embodiments of the system, the at least one of the clinical data and the mathematical modeling predict an approximate time of when the AV fistula has matured.

BRIEF DESCRIPTION OF THE DRAWING

By way of example, specific embodiments of the disclosed devices and methods will now be described, with reference to the accompanying drawings, in which.

DETAILED DESCRIPTION

The present embodiments will now be described more fully hereinafter with reference to the accompanying drawings, in which several exemplary embodiments are shown. The subject matter of the present disclosure, however, may be embodied in many different forms and should not be construed as limited to the embodiments set forth herein. Rather, these embodiments are provided so that this disclosure will be thorough and complete, and willfully convey the scope of the subject matter to those skilled in the art. In the drawings, like numbers refer to like elements throughout.

Figure 1:
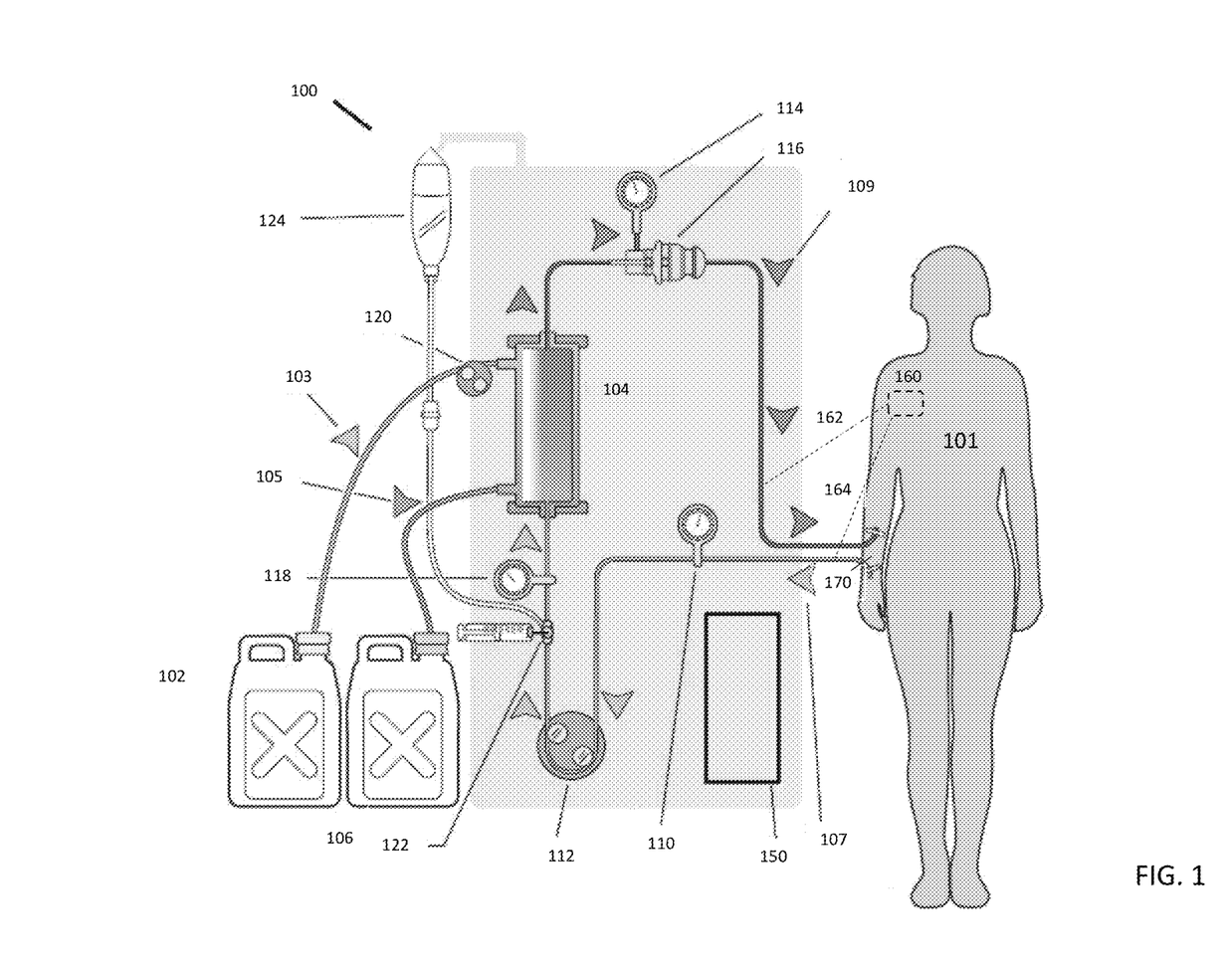
FIG. 1 illustrates an exemplary embodiment of a dialysis system in accordance with the present disclosure.

Referring now to FIG. 1, a diagram of an exemplary embodiment of a dialysis system 700 in accordance with the present disclosure is shown. As described above, a central venous catheter (CVC) may typically be insertable into a patient's internal jugular vein or subclavian vein prior to beginning a hemodialysis treatment, the CVC location being indicated by dashed lines at reference numeral 160 and connecting to the dialysis system 100 by tubing 162, 164, shown in FIG. 1. Dialysis treatment may then be provided to the patient's blood stream via the CVC 160. An AV fistula, its location being indicated by reference numeral 170 of FIG. 1, may be implanted to eventually replace the CVC 160. For example, the AV fistula may be implanted, or created, when the CVC is first inserted or at a later time. A tip of the CVC 160 may be positioned in the superior vena cava just above the entrance to the right atrium of the patient's heart. Accordingly, blood aspirated at this location of the patient's arterial system may be typically blood from the patient's upper body, e.g., arms and head, which may have a lower oxygen saturation (ScvO2) as it travels back to the heart.

The dialysis system 100 may be configured to provide hemodialysis treatment to a patient 101. Treatment may be delivered by a fluid reservoir 102 delivering fresh dialysate to a dialyzer 104 via tubing 103, and reservoir 106 may receive spent dialysate once it has passed through the dialyzer 104 via tubing 105. A hemodialysis operation may filter particulates and/or contaminates from a patient's blood through a patient external filtration device, for example, a dialyzer 104. As the dialysate is passed through the dialyzer 104, so too unfiltered patient blood may be passed into the dialyzer via tubing 107 and filtered blood is returned to the patient via tubing 109. Arterial pressure may be monitored via pressure sensor 110, inflow pressure monitored via sensor 118, and venous pressure monitored via pressure sensor 114. An air trap and detector 116 may ensure that air is not introduced into patient blood as it is filtered and returned to the patient 101. The flow of blood and the flow of dialysate may be controlled via respective pumps, including a blood pump 112 and a fluid pump 120. Heparin 122, a blood thinner, may be used in conjunction with saline 124 to ensure blood clots do not form or occlude blood flow through the system.

Arterial blood, which travels from the heart, may typically have a higher oxygen saturation level than venous blood traveling to the heart, so that when a patient receives an AV fistula to create a left-right shunt, oxygen saturation (ScvO2) levels at the CVC 160 may immediately increase as blood flows from the artery to the vein. This rise in oxygen saturation (ScvO2) levels may be detectable in blood aspirated from the CVC 160, by a blood monitoring system 300. Over time (typically, for example, over the duration of about 3-5 weeks), oxygen saturation levels may gradually increase, from about 60% saturation to about 80%, and may eventually plateau to a substantially constant saturation level.

Figure 3:
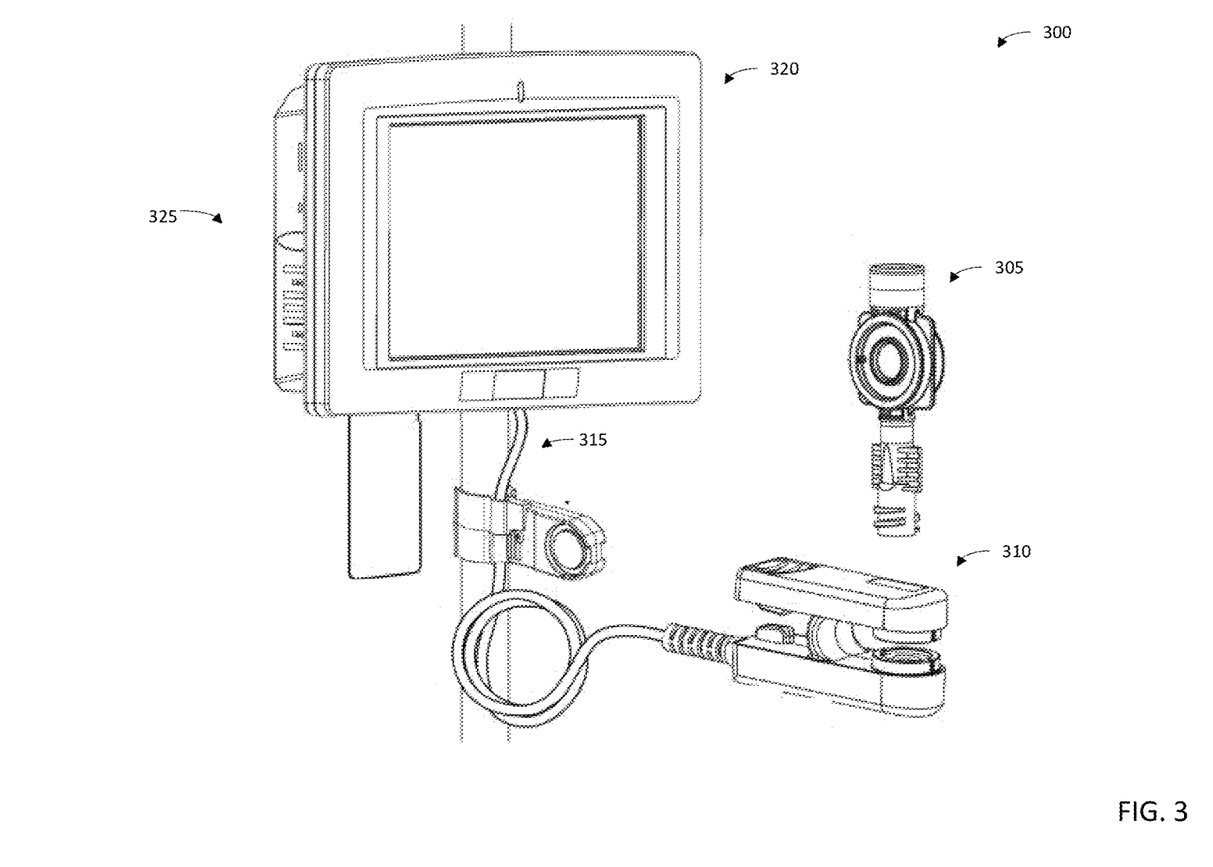
FIG. 3 illustrates an exemplary embodiment of a blood monitoring system in accordance with the present disclosure.

The blood monitoring system 300 may be operatively connected to the dialysis system 100, which may include one or more sensors for detecting and calculating several parameters, including hematocrit and blood oxygen saturation levels (see FIG. 3). In some embodiments, a Crit-Line® Clip Monitor (CLiC) or Crit-Line® Monitor (CLM) systems may be used in connection with a hemodialysis treatment. In various embodiments, the extracorporeal blood circuit may initiate by drawing blood from the arterial side of the fistula, and may terminate with the returning blood to the venous side. In exemplary embodiments, a CLiC or CLM may be arranged on the extracorporeal circuit upstream or downstream of the dialyzer or other components.

Although blood oxygen saturation is described above, the blood measuring system 300 may also measure and monitor hematocrit (for example, the ratio of red blood cells to total blood volume) and/or other physiological parameters from which oxygen saturation may be computed. References to measuring or calculating oxygen saturation should be understood to also encompass these other physiological parameters. It may be advantageous for a hemodialysis patient to monitor hematocrit levels to guide dialysis treatment. Additionally, hematocrit measures blood oxygen carrying capacity, so that the higher a hematocrit value the greater the oxygen carrying capacity.

Figure 4:
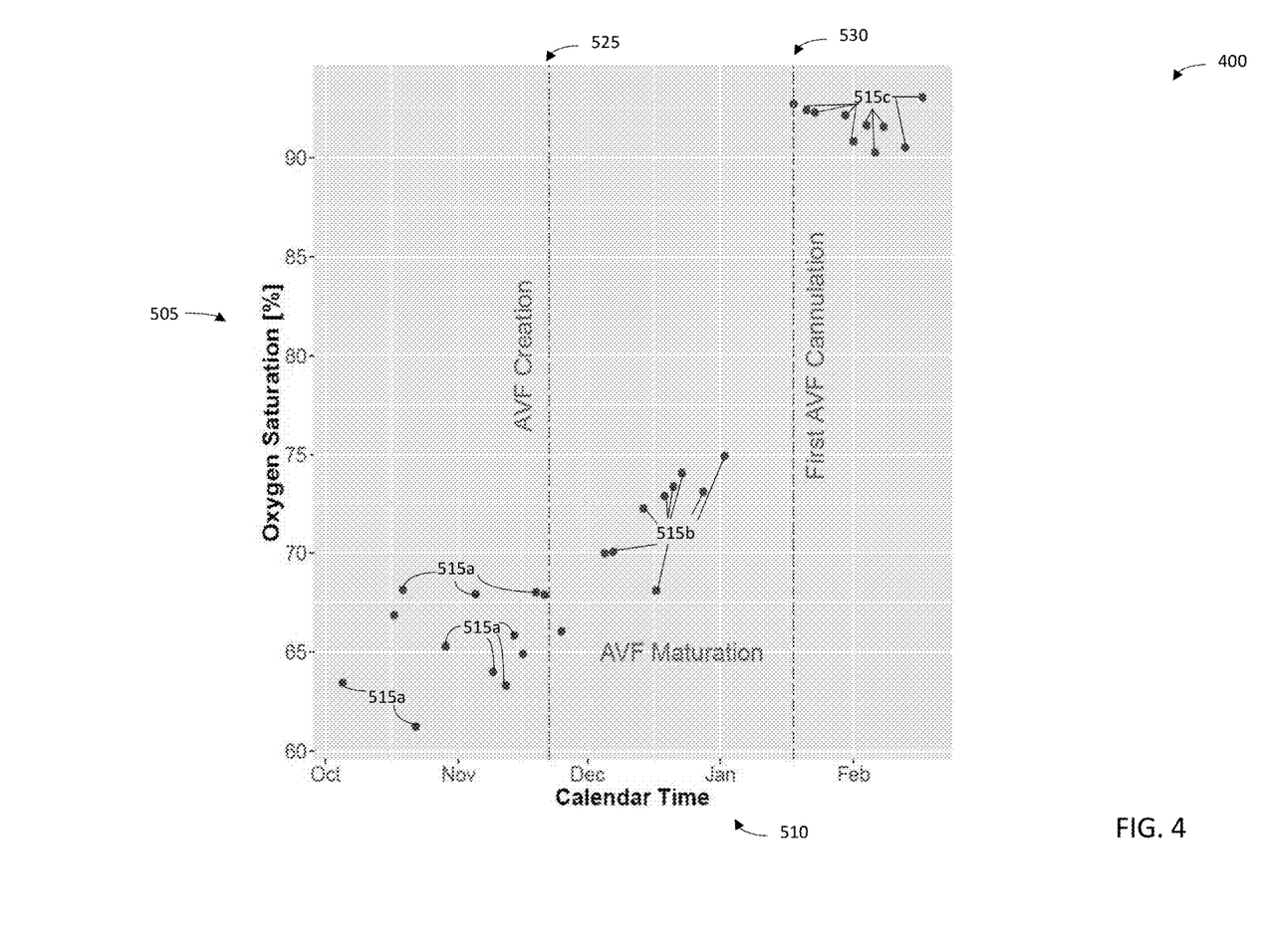
FIG. 4 illustrates a chart of a method of monitoring AV fistula maturation according to some embodiments.

The blood monitoring system 300 may detect a failure of the AV fistula. For example, if instead of detecting an increase of oxygen saturation levels at data points 515b, the data points instead show a decline, or an inability to stabilize over time, or an inability to stabilize at a high enough oxygen saturation level. In some embodiments, an AV fistula failure may be indicated by data points 515b stabilizing at an oxygen saturation level representing a blood flow of the fistula that is too low to permit its use.

Figure 2:
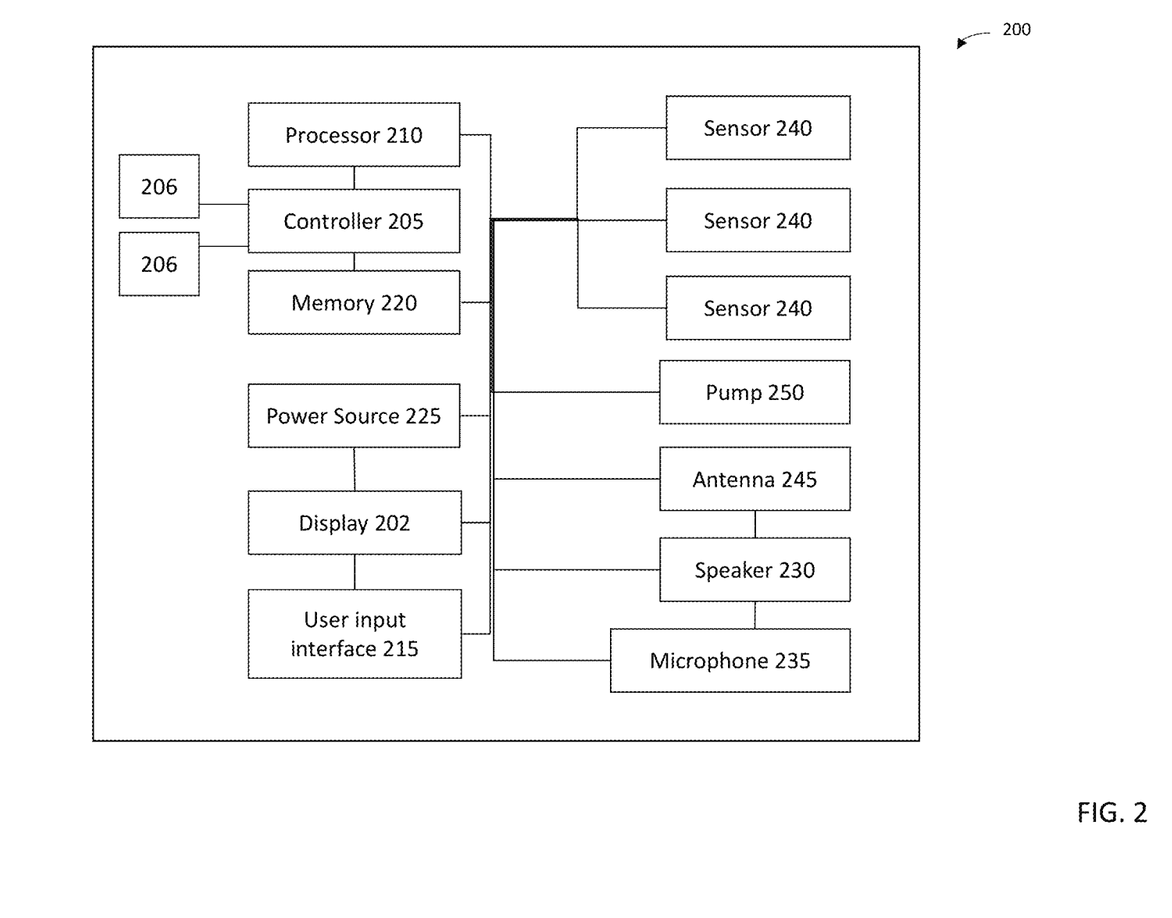
FIG. 2 is a block diagram illustrating an exemplary embodiment of a dialysis machine in accordance with the present disclosure.

Referring to FIG. 1, in some embodiments the dialysis system 100 may include a controller 150, which may be similar to the controller 205 described below with respect to dialysis machine 200 (see FIG. 2). The controller 150 may be configured to monitor fluid pressure readings to identify fluctuations indicative of patient parameters, such as heart rate and/or respiration rate. The controller 150 may also be operatively connected to and/or communicate with additional sensors or sensor systems. Referring to FIG. 2, a schematic of an exemplary embodiment of a dialysis machine 200, and a controller 205 in accordance with the present disclosure are shown. The machine 200 may be a dialysis machine, e.g., a hemodialysis machine, for performing a dialysis treatment on a patient (see FIG. 1). The controller 205 may automatically control execution of a treatment function during a course of dialysis treatment. The controller 205 may be operatively connected to sensors 240 and deliver one or more signals to execute one or more treatment functions, or a course of treatment associated with various treatment systems.

Although FIG. 2 illustrates the components integral to the dialysis machine 200, at least one of the controller 205, processor 210, and memory 220 may be configured to be external and wired or wirelessly connected to the dialysis machine 200, as an individual component of a dialysis system. In some embodiments the controller 205, processor 210 and memory 220 may be remote to the dialysis machine and configured to communicate wirelessly. The controller 205 may be disposed in the machine 100, 200 or may be coupled to the machine 100, 200 via a communication port or wireless communication links, shown schematically as communication element 206. For example, the communication element 206 may operatively connect the dialysis machine 100, 200, to the blood monitoring system 300, or another remote system. Communication between the controller 205 and the treatment system may be bi-directional, whereby the treatment system acknowledges control signals, and/or may provide state information associated with the treatment system and/or requested operations. For example, system state information may include a state associated with specific operations to be executed by the treatment system (e.g., trigger pump to deliver dialysate, trigger pumps and/or compressors to deliver filtered blood, and the like) and a status associated with specific operations (e.g., ready to execute, executing, completed, successfully completed, queued for execution, waiting for control signal, and the like).

The dialysis system or machine 100, 200 may also include at least one pump 250 operatively connected to the controller 205. The controller 205 may also be operatively connected to one or more speakers 230 and one or more microphones 235 disposed in the system or machine 100, 200. The user input interface 215 may include a combination of hardware and software components that allow the controller 205 to communicate with an external entity, such as a patient or other user. Examples of the components that may be employed within the user input interface 215 include keypads, buttons, microphones, touch screens, gesture recognition devices, display screens, and speakers.

As shown in FIG. 2, sensors 240 may be included for detecting and monitoring one or more patient parameters and be operatively connected to at least the controller 205, processor 210, and memory 220. The processor 210 may be configured to execute an operating system, which may provide platform services to application software, e.g., for operating the dialysis machine 200. These platform services may include inter-process and network communication, file system management and standard database manipulation. One or more of many operating systems may be used, and examples are not limited to any particular operating system or operating system characteristic. In some examples, the processor 210 may be configured to execute a real-time operating system (RTOS), such as RTLinux, or a non-real time operating system, such as BSD or GNU/Linux. According to a variety of examples, the processor 210 may be a commercially available processor such as a processor manufactured by INTEL, AMD, MOTOROLA, and FREESCALE. However, the processor 210 may be any type of processor, multiprocessor or controller, whether commercially available or specially manufactured. For instance, according to one example, the processor 210 may include an MPC823 microprocessor manufactured by MOTOROLA.

The memory 220 may include a computer readable and writeable nonvolatile data storage medium configured to store non-transitory instructions and data. In addition, the memory 220 may include a processor memory that stores data during operation of the processor 210. In some examples, the processor memory includes a relatively high performance, volatile, random access memory such as dynamic random access memory (DRAM), static memory (SRAM), or synchronous DRAM. However, the processor memory may include any device for storing data, such as a non-volatile memory, with sufficient throughput and storage capacity to support the functions described herein. Further, examples are not limited to a particular memory, memory system, or data storage system.

The instructions stored on the memory 220 may include executable programs or other code that may be executed by the processor 210. The instructions may be persistently stored as encoded signals, and the instructions may cause the processor 210 to perform the functions described herein. The memory 220 may include information that is recorded, on or in, the medium, and this information may be processed by the processor 510 during execution of instructions. The memory 220 may also include, for example, specification of data records for user timing requirements, timing for treatment and/or operations, historic sensor information, and other databases and the like. The medium may, for example, be optical disk, magnetic disk or flash memory, among others, and may be permanently affixed to, or removable from, the controller 205.

Referring back to FIG. 3, in embodiments, the blood monitoring system 300 may be operatively connectable to the dialysis machine 100, 200. A blood chamber 305 may be connectable to the dialyzer 104, to receive blood aspirated from the CVC 160 or AV fistula 170 via tubing 162, 164. A sensor clip 310 may be positioned substantially perpendicular on the blood chamber 305, for detecting and monitoring blood parameters, e.g., oxygen saturation levels. Sensor data may be provided to a monitor 325 of the blood monitoring system 300. In some embodiments, the monitor 325 may include a processor and a memory or other storage capacity for storing data (not shown), and be operatively connectable to the dialysis machine 100, 200. The monitor 325 may also be connectable to other remote systems for transferring data and other information.

Figure 5:
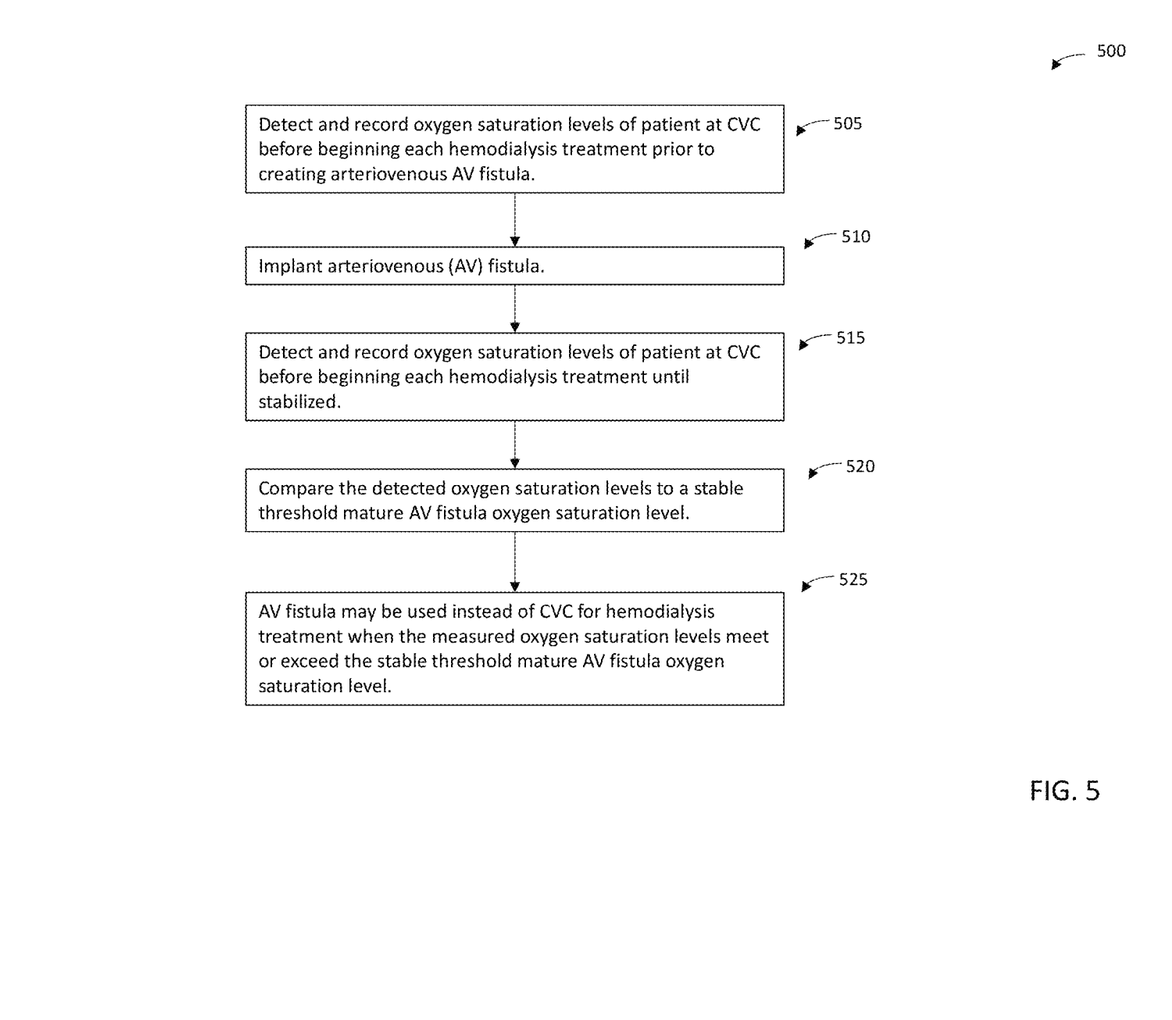
FIG. 5 illustrates a flow diagram of a method of monitoring AV fistula maturation according to some embodiments.

Referring now to FIGS. 4 and 5, an exemplary method for measuring oxygen saturation levels in a hemodialysis treatment is discussed. FIG. 4 illustrates an exemplary embodiment of a chart 400 showing a progression of oxygen saturations measurements over time, and FIG. 5 illustrates a flow chart 500 for an exemplary embodiment of a method for monitoring blood oxygen saturation levels. In embodiments, the method may provide an objective, non-invasive assessment of an AV fistula implanted in a patient. Additionally, the method may allow for monitoring at each hemodialysis treatment to provide a high frequency and continuous monitoring and assessment of the patient. Delivering hemodialysis treatment to a patient may no longer need to rely on a subjective assessment by a medical profession, thereby increasing a standardization of fistula creation and maturation monitoring.

At step 505, a first series of oxygen saturation levels may be detected, monitored, and recorded via the CVC 160 prior to AV fistula 170 creation, so that a baseline level may be known. For example, chart 400 illustrates data points measured of an oxygen saturation percentage level y-axis 505 over time x-axis 510. Data points 515*a* may illustrate a first series of measurements taken prior to or shortly after creating an AV fistula, indicated on the chart time by line 520 and associated with a first series of hemodialysis treatments. Each data point 515*a* may be a measurement taken corresponding to a hemodialysis treatment of the patient. The oxygen saturation levels, e.g., data points 515*a*, may be determined at the beginning of each hemodialysis treatment, e.g., two or three times per week. In embodiments, the data points 515*a* may be recorded by the blood monitoring system 300, and may be analyzed and interpreted for generating a report to be sent to a remote system and/or printed for the patient and the medical professional. For example, the data collection and reporting may be automated by the blood monitoring system and provided to the medical professional for review and analysis.

After a sufficient amount of oxygen saturation levels data collection, the AV fistula 170 may be created at step 510, and defined on the chart 400 by the line 520. A second series of oxygen saturation levels may be determined at the beginning of each hemodialysis treatment at step 515. For example, data points 515*b* may be the second series of oxygen saturation measurements associated with a second series of hemodialysis treatments after the AV fistula 170 was created, but while still utilizing the CVC 160, where each data point 515*b* is a measurement taken prior to a corresponding hemodialysis treatment.

The oxygen saturation measurements may be tracked over time which may indicate an increase in oxygen saturation levels after creation of the AV fistula 170. For example, data points 515*a* may be approximately 60-67% prior to AV fistula creation. During this period of time, the AV fistula 170 may mature, thereby achieving an equilibrium between the artery and vein. As data points 515*b* are measured and charted, the data points 515*b* may also be monitored for changes. For example, as the AV fistula matures and achieves equilibrium, the second series of oxygen saturation levels may level out and plateau at a percentage, or within a range of percentages. This may indicate that the AV fistula is sufficiently mature and ready for use.

At step 520, the second series of oxygen saturation measurements may be compared to a stable threshold AV fistula maturation level. For example, the blood measurement system 300 may store the stable threshold AV fistula maturation level value. An average of the second series of the oxygen saturation measurements may be used for comparison, or a most recent oxygen saturation measurement in the time period may be used for comparison. When the measurements are equal to or greater than the stable threshold, the AV fistula 170 may be mature and ready for use, so that at step 525, the AV fistula 170 may be used for hemodialysis treatment instead of the CVC 160, indicated in the chart 400 by line 530. In some embodiments, the second series of oxygen saturation level measurements may be within a certain range of the stable threshold AV fistula maturation level, for the AV fistula 170 to be considered mature for use. The stable threshold AV fistula maturation level may be determined by clinical data and/or mathematical modeling. In some embodiments, the clinical data and/or the mathematical modeling may predict a date when the AV fistula has matured enough for use. For example, clinical data and modeling may be used to determine an approximate time period of when the AV fistula may be mature enough for use.

Data points 515*c*, e.g., a third series of oxygen saturation levels, may be measured once the AV fistula 170 is in use, each data point 515*c* being a measurement taken prior to a hemodialysis treatment. Unlike the first and second series of data points 515*a*, 515*b* which are collected from the CVC 160, the third series of data points 515*c* are collected from the AV fistula 170. As discussed above, since the AV fistula includes arterial blood having a higher oxygen content, oxygen saturation levels may be higher than earlier oxygen saturation measurements, e.g., 90% or above.

The method described above with respect to the embodiments shown in FIGS. 4 and 5 may be advantageous to provide an objective identification of a stable, mature AV fistula that is ready for cannulation and use as vascular access. Premature use of the AV fistula is thereby prevented, as well as unnecessarily delaying use due to overestimation of the required maturation time. Additionally, the method may provide an independent trigger, e.g., the blood monitoring system 300 may indicate to the dialysis machine 100, 200, or another remote system, to notify a patient or medical professional that the AV fistula has matured and is ready for use.

Some embodiments of the disclosed systems may be implemented, for example, using a storage medium, a computer-readable medium or an article of manufacture which may store an instruction or a set of instructions that, if executed by a machine (i.e., processor or microcontroller), may cause the machine to perform a method and/or operations in accordance with embodiments of the disclosure. In addition, a server or database server may include machine readable media configured to store machine executable program instructions. Such a machine may include, for example, any suitable processing platform, computing platform, computing device, processing device, computing system, processing system, computer, processor, or the like, and may be implemented using any suitable combination of hardware, software, firmware, or a combination thereof and utilized in systems, subsystems, components, or sub-components thereof. The computer-readable medium or article may include, for example, any suitable type of memory unit, memory device, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

As used herein, an element or operation recited in the singular and proceeded with the word "a" or "an" should be understood as not excluding plural elements or operations, unless such exclusion is explicitly recited. Furthermore, references to "one embodiment" of the present disclosure are not intended to be interpreted as excluding the existence of additional embodiments that also incorporate the recited features.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A method for determining an arteriovenous (AV) fistula maturation in a patient, comprising:
    detecting a first series of oxygen saturation levels of the patient at a central venous catheter (CVC) associated with a first series of hemodialysis treatments prior to the AV fistula implantation;
    implanting the AV fistula in the patient;
    detecting a second series of oxygen saturation levels of the patient at the CVC associated with a second series of hemodialysis treatments; and
    comparing the second series of oxygen saturation levels to a stable threshold mature AV fistula oxygen saturation level;
    wherein in response to one or more of the second series of oxygen saturation levels meeting or exceeding the stable threshold mature AV fistula oxygen saturation level, determining the AV fistula is mature.

2. The method according to claim 1, wherein the detected first series of oxygen saturation levels are recorded by a blood monitoring system.

3. The method according to claim 1, wherein the detected second series of oxygen saturation levels are recorded by a blood monitoring system.

4. The method according to claim 1, wherein the first series of oxygen saturation levels include one or more measurements corresponding to a hemodialysis treatment in the first series of hemodialysis treatments.

5. The method according to claim 1, wherein the second series of oxygen saturation levels include one or more measurements corresponding to a hemodialysis treatment in the second series of hemodialysis treatments.

6. The method according to claim 5, wherein in response to a progression of the one or more measurements of the second series of oxygen saturation levels at least one of decreasing, non-stabilizing, or stabilizing below the stable threshold mature AV fistula oxygen saturation level, issuing an alert of a failure of the AV fistula.

7. The method according to claim 5, wherein in response to a progression of the one or more measurements of the second series of oxygen saturation levels increasing, and the second series of oxygen saturation levels are greater than the first series of oxygen saturation levels, validating a maturation of the AV fistula over time.

8. The method according to claim 1, wherein in response to the second series of oxygen saturation levels being lower than the first series of oxygen saturation levels, issuing an alert of a failure of the AV fistula.

9. The method according to claim 1, further comprising monitoring the second series of oxygen saturation levels for at least one of a stabilization or a plateau.

10. The method according to claim 1, wherein the stable threshold mature AV fistula oxygen saturation level is determinable by at least one of clinical data and mathematical modeling.

11. The method according to claim 10, wherein the at least one of the clinical data and the mathematical modeling predict an approximate time of when the AV fistula has matured.

12. A system for determining an arteriovenous (AV) fistula maturation in a patient, comprising:
    a hemodialysis machine;
    a blood monitoring system, the blood monitoring system being configured to:
        detect a first series of oxygen saturation levels of the patient at a central venous catheter (CVC) associated with a first series of hemodialysis treatments prior to the AV fistula implantation;
        detect a second series of oxygen saturation levels of the patient at the CVC associated with a second series of hemodialysis treatments after the AV fistula implantation; and
        compare the second series of oxygen saturation levels to a stable threshold mature AV fistula oxygen saturation level;
        wherein in response to one or more of the second series of oxygen saturation levels meeting or exceeding the stable threshold mature AV fistula oxygen saturation level, determining the AV fistula is mature.

13. The system according to claim 12, wherein the detected first series of oxygen saturation levels are recordable by the blood monitoring system.

14. The system according to claim 12, wherein the detected second series of oxygen saturation levels are recordable by the blood monitoring system.

15. The system according to claim 12, wherein the first series of oxygen saturation levels include one or more measurements corresponding to a hemodialysis treatment in the first series of hemodialysis treatments.

16. The system according to claim 10, wherein the second series of oxygen saturation levels include one or more measurements corresponding to a hemodialysis treatment in the second series of hemodialysis treatments.

17. The system according to claim 16, wherein in response to a progression of the one or more measurements of the second series of oxygen saturation levels at least one of decreasing, non-stabilizing, or stabilizing below the stable threshold mature AV fistula oxygen saturation level, issuing an alert of a failure of the AV fistula.

18. The system according to claim 16, wherein in response to a progression of the one or more measurements of the second series of oxygen saturation levels increasing, and the second series of oxygen saturation levels are greater than the first series of oxygen saturation levels, validating a maturation of the AV fistula over time.

19. The system according to claim 10, wherein in response to the second series of oxygen saturation levels being lower than the first series of oxygen saturation levels, sending an alert of a failure of the AV fistula.

20. The system according to claim 10, further comprising monitoring the second series of oxygen saturation levels for at least one of a stabilization or a plateau.

21. The system according to claim 10, wherein the stable threshold mature AV fistula oxygen saturation level is determinable by at least one of clinical data and mathematical modeling.

22. The system according to claim 21, wherein the at least one of the clinical data and the mathematical modeling predict an approximate time of when the AV fistula has matured.

* * * * *